(12) United States Patent
Seyedin et al.

(10) Patent No.: US 8,444,968 B2
(45) Date of Patent: May 21, 2013

(54) CARTILAGE REPAIR METHODS

(75) Inventors: Mitchell S. Seyedin, Monte Sereno, CA (US); Matthew Matava, St. Louis, MO (US)

(73) Assignee: Isto Technologies, Inc., St. Louis, MO (US)

(*) Notice: Subject to any disclaimer, the term of this patent is extended or adjusted under 35 U.S.C. 154(b) by 1404 days.

(21) Appl. No.: 11/635,265

(22) Filed: Dec. 7, 2006

(65) Prior Publication Data

US 2007/0128155 A1 Jun. 7, 2007

Related U.S. Application Data

(60) Provisional application No. 60/748,027, filed on Dec. 7, 2005.

(51) Int. Cl.
*A01N 65/00* (2009.01)

(52) U.S. Cl.
USPC ........ 424/93.7; 106/162.2; 424/462; 435/180

(58) Field of Classification Search
USPC ....................................................... 424/93.7
See application file for complete search history.

(56) References Cited

U.S. PATENT DOCUMENTS

| | | | |
|---|---|---|---|
| 4,438,102 A | 3/1984 | Ganci | |
| 4,692,371 A | 9/1987 | Morman et al. | |
| 4,957,744 A | 9/1990 | Della Valle et al. | |
| 5,290,552 A | 3/1994 | Sierra et al. | |
| 5,597,897 A | 1/1997 | Ron et al. | |
| 5,700,289 A | 12/1997 | Breitbart et al. | |
| 5,736,372 A | 4/1998 | Vacanti et al. | |
| 5,769,899 A | 6/1998 | Schwartz et al. | |
| 5,842,477 A | 12/1998 | Naughton et al. | |
| 5,855,608 A | 1/1999 | Brekke et al. | |
| 5,916,585 A | 6/1999 | Cook et al. | |
| 5,972,385 A | 10/1999 | Liu et al. | |
| 6,051,701 A | 4/2000 | Cialdi et al. | |
| 6,281,256 B1 | 8/2001 | Harris et al. | |
| 6,303,585 B1 | 10/2001 | Spiro et al. | |
| 6,328,765 B1 | 12/2001 | Hardwick et al. | |
| 6,339,074 B1 | 1/2002 | Cialdi et al. | |
| 6,344,488 B1 | 2/2002 | Chenite et al. | |
| 6,395,253 B2 * | 5/2002 | Levy et al. ................... | 424/1.25 |
| 6,454,811 B1 | 9/2002 | Sherwood et al. | |
| 6,579,978 B1 | 6/2003 | Renier et al. | |
| 6,596,274 B1 | 7/2003 | Abatangelo et al. | |
| 6,626,950 B2 | 9/2003 | Brown et al. | |
| 6,673,285 B2 | 1/2004 | Ma | |
| 6,689,747 B2 | 2/2004 | Filvaroff et al. | |
| 6,696,073 B2 | 2/2004 | Boyce et al. | |
| 6,949,252 B2 | 9/2005 | Mizuno et al. | |
| 7,087,745 B1 | 8/2006 | Pallado et al. | |
| 7,446,131 B1 | 11/2008 | Liu et al. | |
| 2002/0004225 A1 | 1/2002 | Hart et al. | |
| 2002/0064559 A1 | 5/2002 | Lee et al. | |
| 2004/0001879 A1 | 1/2004 | Guo et al. | |
| 2004/0033212 A1 | 2/2004 | Thomson et al. | |
| 2004/0078090 A1 | 4/2004 | Binette et al. | |
| 2004/0126405 A1 | 7/2004 | Sahatjian et al. | |
| 2004/0138664 A1 | 7/2004 | Bowman | |
| 2005/0142163 A1 | 6/2005 | Hunter et al. | |
| 2006/0002979 A1 | 1/2006 | Ashammakhi et al. | |
| 2006/0008530 A1 * | 1/2006 | Seyedin et al. ............... | 424/486 |
| 2007/0128155 A1 | 6/2007 | Seyedin et al. | |

FOREIGN PATENT DOCUMENTS

| | | |
|---|---|---|
| WO | 9300050 | 1/1993 |
| WO | 9401468 | 1/1994 |
| WO | 9531157 | 11/1995 |
| WO | 9628539 | 9/1996 |
| WO | 0101895 | 1/2001 |
| WO | 0135968 | 5/2001 |
| WO | 02072662 | 9/2002 |
| WO | 02076335 | 10/2002 |
| WO | 03039615 | 5/2003 |
| WO | 2006058221 | 6/2006 |

OTHER PUBLICATIONS

Gombotz and Pettit, 1995. Biodegradable polymers for protein and peptide drug delivery. Bioconjugate Chem., vol. 6:332-351.*
Benjamin, M. et al, Biology of Fibrocartilage Cells, Int. Rev. Cytol., 2004, pp. 1-45, vol. 233.
Fu, F.H. et al, Autologous chondrocyte implantation versus debridement for treatment of full-thickness chondral defects of the knee: an observational cohort study with 3-year follow-up, Am. J. Sports Med., 2005, pp. 1658-1666, vol. 33, No. 11.
Gilbert, J.E., Current treatment options for the restoration of articular cartilage, Am. J. Knee Surg., 1998, pp. 42-46, vol. 11, No. 1.

(Continued)

*Primary Examiner* — Susan Hanley
*Assistant Examiner* — Nghi Nguyen
(74) *Attorney, Agent, or Firm* — Polsinelli Shughart PC

(57) ABSTRACT

The present application discloses methods for repairing hyaline cartilage defects. The methods comprise a combination of introducing autologous bone mesenchymal stem cells to a joint, and applying to the joint a membrane comprising a polyester entangled with a polysaccharide. In some aspects, the bone mesenchymal stem cells are mesenchymal stem cells originating in bone underlying the joint. In these aspects, contact between the joint and the mesenchymal stem cells can be effected by introducing apertures through the bone using standard surgical techniques such as microfracture, abrasion, or drilling. Cartilage which forms in response to application of these methods is hyaline cartilage rather than fibrocartilage.

9 Claims, No Drawings

OTHER PUBLICATIONS

Gross, A.E., Cartilage resurfacing: filling defects, J. Arthroplasty, 2003, pp. 14-17, vol. 18, No. 3, Suppl. 1.

Helmsworth, T.F. et al, Molecular surgery of the basement membrane by the argon laser, 1990, pp. 576-583, vol. 10, No. 6.

Hunziker, E.B., Articular cartilage repair: basic science and clinical progress. A review of the current status and prospects, Osteoarthritis Cartilage, 2003, pp. 432-463, vol. 10, No. 6.

Minas, T. et al, Current concepts in the treatment of articular cartilage defects, Orthopedics, 1997, pp. 525-538, vol. 20, No. 6.

Steadman, J.R. et al, Microfracture: surgical technique and rehabilitation to treat chondral defects, Clin. Orthop. Relat. Res., 2001, pp. S362-S369, Suppl. 391.

Stone, K.R. et al., New Techniques For Cartilage Repair and Replacement, www.stoneclinic.com/newtechcartrep3.htm, 9 pages.

Vangsness, C.T. et al, Restoring articular cartilage in the knee, Am. J. Orthop., 2004, pp. 29-34, vol. 33, Suppl. 2.

De Gennes, P.G., Reptation of a Polymer Chain in the Presence of Fixed Obstacles, Journal of Chemical Physics, 1971, pp. 572-579, vol. 55, No. 2.

Edwards, S.F., The statistical mechanics of polymerized material, Proc. Phys. Cos, 1967, pp. 9-16, vol. 92.

International Search Report dated Sep. 16, 2008 regarding PCT/US2007/70631, 6 pages.

International Search Report regarding European National Application No. 05812025.4, issued Dec. 14, 2009, 1 page.

Examination Report regarding Australian Application No. 2005287402 issued Aug. 26, 2009, 2 pages.

Uematsu, K. et al, Cartilage regeneration using mesenchymal stem cells and a three-dimensional poly-lactic-glycolic acid (PLGA) scaffold, Biomaterials, 2005, pp. 4273-4279, vol. 26, No. 20.

English translation of claims for Japanese Application No. 7-157439 as provided by foreign associate on Jan. 2011, 4 pages.

Notice of Allowance and Fees Due regarding U.S. Appl. No. 11/179,425 with the mailing date of May 6, 2011, 13 pages.

Amiel, D. et al, Rib Perichondrial Grafts for the Repair of Full-Thickness Articular-Cartilage Defects, J. Bone Joint Surg., 1985, pp. 911-920, vol. 67A.

Blein Sella, O. and Adolphe, M., Rabbit Articular Chondrocyte Functional Toxicity Test, Methods in Molecular Biology, 1995, pp. 169-175, vol. 43.

Dietz, U. et al, Alterations of Collagen mRNA Expression During Retinoic Acid Induced Chondrocyte Modulation: Absence of Untranslated α1(I) mRNA in Hyaline Chondrocytes, J. Cellular Biochemistry, 1993, pp. 57-68, vol. 52.

Fukuzaki, H. et al, In vivo characteristics of low molecular weight copolymers composed of L-lactic acid and various DL-hydroxy acids as biodegradable carriers for drug delivery systems, Biomaterials, 1990, pp. 441-446, vol. 11.

Hollinger, J., Preliminary report on the osteogenic potential of a biodegradable copolymer of polyactide (PLA) and polyglycolide (PGA), J. Biomedical Materials Research, 1983, pp. 71-82, vol. 17.

Hyaluronan-Modified Surfaces for Medical Devices, www.devicelink.com/grabber.php3?URL=http://www.devicelink.com/mddi/archive . . . , MD&D column, 1999, print date of Oct. 14, 2005, 15 pages.

Jalil, R. and Nixon, J.R., Biodegradable poly(lactic acid) and poly(lactide-co-glycolide) microcapsules: problems associated with preparative techniques and release properties, J. Microencapsulation, 1990, pp. 297-325, vol. 7, No. 3.

Kuettner, K.E., Biochemistry of Articular Cartilage in Health and Disease, Clin. Biochem, 1992, pp. 155-163, vol. 25.

Kuo, J., et al, Chemical Modification of Hyaluronic Acid by Carbodiimides, Bioconjugate Chem, 1991, pp. 232-241, vol. 2.

Mason, M. et al, Attachment of hyaluronic acid to polypropylene, polystyrene, and polytetrafluoroethylene, Biomaterials, 2000, pp. 31-36, vol. 21.

Sierra, D.H. et al, Fibrin-collagen Adhesive Drug Delivery System for Tumor Therapy, Trans. Soc. Biomater., 1993, pp. 257, vol. 16.

Zhao, X.B., et al, Synthesis and characterization of a novel double crosslinked hyaluronan hydrogel, J. Mater. Sci Mater. Med, 2002, pp. 11-16, vol. 13.

Office Action issued Mar. 31, 2010 regarding U.S. Appl. No. 11/448,701, 27 pages.

Office Action issued Dec. 9, 2010 regarding U.S. Appl. No. 11/448,701, 19 pages.

Office Action issued Oct. 2, 2008 regarding U.S. Appl. No. 11/448,701, 15 pages.

Office Action issued Aug. 27, 2010 regarding U.S. Appl. No. 11/179,425, 17 pages.

Office Action issued Dec. 23, 2009 regarding U.S. Appl. No. 11/179,425, 17 pages.

Office Action issued Feb. 23, 2009 regarding U.S. Appl. No. 11/179,425, 25 pages.

Office Action issued Apr. 15, 2010 regarding U.S. Appl. No. 11/179,425, 16 pages.

Office Action issued Nov. 29, 2010regarding U.S. Appl. No. 11/179,425, 9 pages.

Benesova, K. et al, Stability Evaluation of n-ALKYL Hyaluronic Acid Derivates by DSC and TG Measurement, J. of Thermal Analysis and Calorimetry, 2006, pp. 341-348, vol. 83.

Wang, Z.G. et al, Morphological development in absorbable poly(glycolide), poly(glycolide-co-lactide) and poly (glycolide-co-caprolactone) copolymers during isothermal crystallization, Polymer, 2000, pp. 621-628, vol. 41.

Office Action regarding Japanese Patent Application No. 2007-521541 issued Dec. 22, 2010, 7 pages.

European Search Opinion regarding European Application No. 06839104.4 issued Dec. 23, 2009, 19 pages.

* cited by examiner

CARTILAGE REPAIR METHODS

CROSS-REFERENCE TO RELATED APPLICATIONS

This application claims the benefit of the filing date of U.S. provisional application Ser. No. 60/748,027 filed on Dec. 7, 2005.

INTRODUCTION

Defects of articular joints are significant sources of pain, discomfort and disability. These defects, such as full-thickness chondral defects, can be associated with diseases such as osteoarthritis, injury and/or degeneration of articular cartilage. Morbidity associated with defects of hyaline cartilage comprised by articular joints are responsible for significant economic, health and social costs.

Current treatments for repair or amelioration of joint problems include microfracture, abrasion and drilling. These interventions involve exposing a joint containing a defect to mesenchymal stem cells. As a result of such interventions, the mesenchymal stem cells can infiltrate the defect, and differentiate into fibrocartilage over time. However, fibrocartilage has a structure and molecular composition distinct from that of hyaline cartilage (Benjamin, M., et al., International Review of Cytology 233: 1-45, 2004). Fibrocartilage generally provides only short-term improvement, typically lasting less than two years. (See, e.g., Hunziker, E. B., Osteoarthritis and Cartilage 10: 432-463, 2001; Steadman, J. R., et al., Clinical Orthopaedics and Related Research 391 S: S362-S369, 2001; Diduch, D. R., et al., http://www.orthopedictechreview.com/issues/novdec02/pg24.htm; Stone, K. R., et al., http://www.stoneclinic.com/newtechcartrep3.htm; Fu, F. H., et al., Amer. J. Sports Medicine 33: 1658-1666, 2005; Minas, T., et al., Orthopedics 20: 525-538, 1997; Gilbert, J. E., Amer. J. Knee Surgery 11: 42-46, 1998; Gross, A. E., J. Arthroplasty 18: 14-17, 2003.) Alternative treatments are, therefore, needed.

SUMMARY

In view of the need for therapeutic interventions to treat chondral defects, the present inventors disclose herein methods for repairing a hyaline cartilage defect in a joint in a mammal such as a human patient in need of treatment. These methods comprise a combination of infiltrating a joint in need of repair with autologous mesenchymal stem cells and applying to the joint a membrane comprising a polyester entangled with a polysaccharide. Application of these methods can result in deposition of hyaline cartilage instead of fibrocartilage at a defect site, and thereby provide long-term improvement, including complete repair, of a joint defect.

In various configurations of the present teachings, the mesenchymal stem cells can be bone mesenchymal stem cells autologous to the mammal, and can originate in a bone marrow cavity underlying the joint in need of repair. In some aspects, the joint in need of repair can comprise a full-thickness chondral defect. The joint can be any articular joint comprising hyaline cartilage, such as, without limitation, a knee joint.

In various embodiments, the methods comprise introducing at least one aperture into the bone underlying the joint. The at least one aperture can be sufficiently large to make possible migration of mesenchymal stem cells from a marrow cavity of the bone to the joint, and can thereby make possible establishment of contact between the mesenchymal stem cells and the joint. In various configurations, introduction of an aperture into a joint can be achieved by any method known to skilled artisans, such as, for example, abrasion, microfracture, or drilling of the bone. When abrasion is used, the abrading can comprise performing abrasion arthroplasty.

In various aspects of the present teachings, a membrane comprising a polyester entangled with a polysaccharide can have a thickness of at least about 0.5 mm up to about 3 mm. In some aspects, a membrane can be applied to a joint prior to aperture introduction, while in other aspects, aperture introduction can precede membrane application.

Membranes of the present teachings include a polyester entangled with a polysaccharide. In various aspects, a polyester which comprises a membrane can be composed of polylactic acid, polyglycolic acid, or a co-polymer comprising polylactic acid and polyglycolic acid. In various aspects, the polylactic acid and polyglycolic acid can be in a weight ratio of from about 5:1 to about 2:1, such as a weight ratio of about 3:1.

In various configurations, membranes of the present teachings further include at least one polysaccharide. In various aspects, a polysaccharide can be hyaluronic acid, chondroitin sulfate, dermatan sulfate, keratan sulfate, heparan, heparan sulfate, dextran, dextran sulfate, alginate, and a combination thereof. In some configurations, the polysaccharide can be hyaluronic acid. In various aspects, the polyester and polysaccharide can be in a weight ratio of from 99:1 to 1:99, and in certain configurations, the weight ratio of polyester to polysaccharide can be from about 9:1 to about 1:9. In various configurations, a polyester can be entangled with a polysaccharide using methods set forth in U.S. patent application Ser. No. 11/179,425, filed Jul. 11, 2005.

In some embodiments, methods of the present teachings can further include securing a membrane as described herein to a joint in need of repair. In various aspects, a membrane can be secured to a joint using at least one fastener. A fastener of these configurations can be any fastener known to skilled artisans, such as, without limitation, a biocompatible glue, a suture, a tissue weld, a dart, a staple, a screw, and a tack. In certain aspects, a biocompatible glue can be a fibrin glue.

In certain embodiments of the present teachings, a membrane described herein can further comprise at least one growth factor. Examples of a growth factor which can be comprised by a membrane include, without limitation, TGF-β, a bone morphogenetic protein, a growth differentiation factor, ADMP-1, a fibroblast growth factor, a hedgehog protein, an insulin-like growth factor, a platelet-derived growth factor, an interleukin, a colony-stimulating factor, and an activin. In addition, in some embodiments, a membrane can further comprise at least one collagen.

In various configurations, the present teachings set forth methods for repairing a full-thickness chondral defect in a joint of a patient in need of treatment. These methods comprise both microfracturing bone underlying the joint, and applying to the joint a membrane comprising a polyester co-polymer comprising polylactic acid and polyglycolic acid in a weight ratio of from about 5:1 to about 2:1, wherein the polyester is entangled with hyaluronic acid. A membrane of these configurations can have a thickness of at least about 0.5 mm up to about 3 mm. These methods can further comprise anchoring the membrane to the joint.

In addition, the present teachings set forth methods for repair of a full-thickness chondral defect in a joint of a patient in need of treatment. These methods comprise introducing at least one aperture through bone underlying the joint, wherein the at least one aperture makes possible migration of mesenchymal stem cells comprised by a marrow cavity of the bone to the joint, and applying to the joint a membrane comprising hyaluronic acid entangled with a polyester co-polymer comprising polylactic acid and polyglycolic acid in a weight ratio of from about 5:1 to about 2:1, wherein the membrane has a thickness of at least about 0.5 mm up to about 3 mm. In some configurations, the methods further include securing the membrane to the joint.

DETAILED DESCRIPTION

The present inventors have devised methods for repairing hyaline cartilage comprised by a joint. These methods entail a) infiltrating a joint in need of repair with autologous mesenchymal stem cells and b) applying to the joint a membrane comprising a polyester entangled with a polysaccharide. As used herein, the term "mesenchymal stem cells" refers to pluripotent cells which originate within juvenile or adult mesenchymal tissue. Accordingly, for example, autologous mesenchymal stem cells can be autologous bone mesenchymal stem cells, i.e., autologous mesenchymal stem cells which originate within the marrow cavity of a bone.

In various embodiments of the present teachings, membranes comprising a polyester entangled with a polysaccharide, and methods of making such membranes, are described in U.S. patent application Ser. No. 11/179,425, "Tissue Matrix System," filed Jul. 11, 2005, Publication No. 20060008530 A1, which is incorporated herein by reference in its entirety. "Entanglement" and related terms, as used herein, refers to a state of polymers in melts or concentrated solutions above the overlap concentration, in which polymers interpenetrate one another and motion of the molecules is restricted to movement along a 'virtual tube' which surrounds each molecule.

The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

The present methods of joint repair can be applied to any body joint comprising hyaline cartilage, such as, but not limited to, a joint of a knee, an elbow, an ankle, a shoulder, a jaw or a wrist. Furthermore, the methods can be used with both humans and animals having joint defects, including, without limitation, a mammal such as companion animal or farm animal (e.g., a cat, a dog, a sheep, a cow, a goat, a pig, or a horse). Defects which can be treated can be any form of joint defect involving loss of or damage to hyaline cartilage, such as, but not limited to, a full-thickness defect, a partial-thickness defect, an age-related degenerative disease defect such as osteoarthritis, a congenital defect, or an injury resulting from trauma.

Treatment of a joint defect using the methods disclosed herein can effect repair of a cartilage defect in which new cartilage that deposits following intervention is hyaline cartilage rather than fibrocartilage. The methods comprise contacting the joint with cells which can differentiate into chondrocytes, such as mesenchymal stem cells comprised by bone, and applying the joint a membrane comprising polyester entangled with a polysaccharide such as hyaluronic acid. Most conveniently, such mesenchymal stem cells can be autologous mesenchymal stem cells originating in the bone underlying the damaged joint, although mesenchymal stem cells from other bones can be used as well. Contact between the damaged joint and autologous mesenchymal stem cells from the underlying bone can be effected most readily by introducing one or more apertures into the bone underlying the defective joint. Such apertures need be at least large enough to allow passage of the mesenchymal stem cells from the bone mesenchyme to the joint. Several well-established procedures can be used to form such passages, such as, without limitation, abrasion (such as abrasion arthroplasty), microfracture, and drilling of the bone. These and other treatment procedures are well known to skilled artisans, and are described in references such as Steadman, J. R. et al., Clinical Orthopaedics and Related Research 391 S: S362-S369, 2001, Rodrigo J. J., et al., Osteoarticular injuries of the knee. pp. 2077-2082, In: Chapman, M. W. (ed): Operative Orthopaedics, Vol. 3, 2nd Ed. Lippincott, Philadelphia, Pa., 1993; Tippet J. W., Articular cartilage drilling and osteotomy in osteoarthritis of the knee, pp. 325-339, in: McGinty, J. B. (ed): Operative Arthroscopy. Raven Press, New York, N.Y., 1991; Vangsness, C. T., et al., Amer. J. Orthop. 33 (2 Suppl): 29-34, 2004; Textbook of Arthroscopy, Miller, M. D. et al., ed. Saunders, 2004; The Adult Knee, Callaghan, J. J. et al., ed., Lippincott Williams & Wilkins, 2003; Operative Treatment of Elbow Injuries, Baker, C. L., et al., ed., Springer, 2002; Osteoarthritis: Fundamentals and Strategies for Joint-preserving Treatment, Grifka, J. J., et al., ed., Springer, 2000; Reconstructive Surgery of the Joints, Morrey, B. F., et al., ed., Churchill Livingstone, 1996; Operative Arthroscopy, McGinty, J. B., et al., ed., Lippincott-Raven, 1996; The Knee, Scott, W. N., ed., Mosby-Year Book, 1994; Surgical Repair and Reconstruction in Rheumatoid Disease, Benjamin, A., et al., Spring-Verlag, 1993; The Knee: Form, Function, Pathology, and Treatment; Larson, R. L., et al., ed., W.B. Saunders, 1993; and O'Connor's Textbook of Arthroscopic Surgery, Shahriaree, H., ed., J. B. Lippincott, 1992. Without being limited by theory, it is believed that following introduction of passages into the bone, mesenchymal stem cells can migrate out from the bone marrow cavity through the passages, and populate the joint. Exposure of the mesenchymal stem cells to the local environment of the joint leads to differentiation of the stem cells into cartilage-forming chondrocytes. In the presence of a membrane comprising a polyester and a polysaccharide such as hyaluronic acid, the chondrocytes produce hyaline cartilage rather than fibrocartilage. The introduction of the cells under these conditions can thereby restore the cartilage of a defective joint to a state more closely resembling that of the joint pre-injury.

In various configurations, a membrane utilized in the present methods comprises a polyester entangled with a polysaccharide such as hyaluronic acid. A membrane can have a thickness of at least about 0.5 mm up to about 3 mm. These membranes can be prepared by methods set forth in U.S. patent application Ser. No. 11/179,425, filed Jul. 11, 2005, which is hereby incorporated by reference in its entirety. As described therein, a polyester of a membrane can comprise polylactic acid, polyglycolic acid, or a co-polymer of polylactic acid and polyglycolic acid (a "PLA/PLG polymer"). In some aspects, the weight ratio of polylactic acid to polyglycolic acid in a PLA/PLG polymer can be from about 5:1 to about 2:1, for example about 3:1. In addition, a polysaccharide comprised by a membrane can be hyaluronic acid, chondroitin sulfate, dermatan sulfate, keratan sulfate, heparan, heparan sulfate, dextran, dextran sulfate, alginate, or a combination thereof, and in some embodiments, the polysaccharide can be hyaluronic acid. As used herein, the term "hyaluronic acid" can refer to the free acid form of hyaluronic acid, a salt of hyaluronic acid such as sodium hyaluronate, or a combination thereof. In some configurations, the hyaluronic acid can be a commercially available hyaluronic acid, such as a hyaluronic acid distributed by Lifecore Biomedical, Inc, Chaska, Minn. and can have a weight average molecular weight of from about 100,000 to about 2,000,000 Daltons. In a non-limiting example, the hyaluronic acid can be sodium hyaluronate having an average molecular weight of about 1,700,000. In various aspects, the weight ratio of the polyester to the polysaccharide can be from 99:1 to 1:99. In some configurations, the ratio of the polyester to the polysaccharide can be from about 9:1 to about 1:9.

In various aspects of the present teachings, a skilled artisan, such as, for example, an orthopaedic surgeon, can shape a membrane into a shape appropriate for a particular joint defect. The appropriate shape can be determined according to principles well known to skilled artisans, for example, by following guidelines for medical treatment of chondral defects set forth in standard texts such as those listed above.

In some configurations, methods of the present teachings include securing the membrane to the joint. Securing the membrane to the joint can be part of the surgical intervention in the treatment of a patient. Accordingly, in various aspects, a skilled artisan such as an orthopaedic surgeon can immobilize a membrane at the site of defect in a patient, using at least one fastener, and thereby retain the membrane at the site. Such retention of the membrane can promote the formation of hyaline cartilage by chondrocytes differentiated from mesenchymal stem cells. Examples of a fastener that can be used in the present methods include, without limitation, a biocompatible glue, a suture, a tissue weld, a dart, a staple, a screw, a tack, and a combination thereof. In some aspects, a biocompatible glue can be a fibrin glue, such as a fibrin sealant. A non-limiting example of a biocompatible glue that can be used with the present teachings is a fibrin sealant manufactured by Oesterreichisches Institut Fuer Haemoderivate G.M.B.H. in Vienna, Austria and distributed by Baxter Healthcare Corporation, Glendale, Calif. under the brand name TISSEEL® VH. Non-limiting examples of other fasteners which can be used instead of, or in addition, a biocompatible glue include sutures, tissue welds such as described in Helmsworth, T. F., et al., Laser Surgery Medicine 10: 576-583, 1990, staples, darts, pins and tacks. In some aspects, a fastener can comprise a biocompatible material such as, without limitation, a PLA/PLG polymer.

In some aspects, a membrane of the present teachings can further comprise one or more growth factors. Without being limited by theory, it is believed that certain growth factors can promote formation of hyaline cartilage by promoting differentiation of mesenchymal stem cells into hyaline cartilage-forming chondrocytes, and can thereby speed healing. Non-limiting examples of growth factors which can be incorporated into a membrane of the present teachings include a fibroblast growth factor such as basic fibroblast growth factor (bFGF), a transforming growth factor such as transforming growth factor-β (TGF-β), a bone morphogenetic protein (BMP) such as BMP-2, ADMP-1, a hedgehog protein, an insulin-like growth factor, a platelet-derived growth factor, an interleukin, a colony-stimulating factor, and an activin. Furthermore, in some configurations, a membrane can comprise, in addition to or instead of a growth factor, a collagen such as type I collagen or type II collagen. Amounts of a growth factor or collagen to be incorporated into a membrane can be determined by a skilled artisan without undue experimentation.

Accordingly, in various configurations, the present teachings set forth methods for repairing a full-thickness chondral defect in a joint of a patient in need of treatment. These methods comprise both microfracturing bone underlying the joint, and applying to the joint a membrane comprising a polyester co-polymer comprising polylactic acid and polyglycolic acid in a weight ratio of from about 5:1 to about 2:1, wherein the polyester is entangled with hyaluronic acid. A membrane of these configurations can have a thickness of at least about 0.5 mm up to about 3 mm. These methods can further comprise anchoring the membrane to the joint. A joint of these configurations can be any joint comprising articular cartilage, such as a joint of a long bone, for example a knee joint comprising articular cartilage of a femur. In these configurations, the microfracturing can precede the application of a membrane, or vice versa.

Furthermore, the present teachings set forth methods for repair of a full-thickness chondral defect in a joint of a patient in need of treatment. These methods comprise a) introducing at least one aperture through bone underlying the joint, wherein the at least one aperture makes possible migration of mesenchymal stem cells comprised by a marrow cavity of the bone to the joint, and b) applying to the joint a membrane comprising hyaluronic acid entangled with a polyester co-polymer comprising polylactic acid and polyglycolic acid in a weight ratio of from about 5:1 to about 2:1, wherein the membrane has a thickness of at least about 0.5 mm up to about 3 mm. The methods can further comprise securing the membrane to the joint, using attachments methods and devices well known to skilled artisans.

In these methods, introduction of at least one aperture can precede application of a membrane to the joint, or application of a membrane to the joint can precede the introduction of at least one aperture. Furthermore, in these methods, a membrane can be secured to a joint by applying at least one fastener to the membrane and to the joint. Non-limiting examples of a fastener include a biocompatible glue such as a fibrin glue, a suture, a tissue weld, a dart, a staple, a screw, and a tack. A fastener of these methods can be made of a bioabsorbable material such as a polyester, or of non-absorbable material such as a biocompatible metal. Accordingly, in non-limiting example, a fastener can be an absorbable suture which passes through both the membrane and a joint, and thereby secures apposition of the membrane to the joint. Furthermore, in non-limiting example, the attaching can comprise glueing the membrane to the joint.

In various aspects, the methods described herein can be applied to any mammal, including a human patient in need of treatment. In addition to a human, the methods can be applied to any mammal, such as, in non-limiting example a companion animal such as a cat or dog, or a farm animal such as a horse, a bovine, a goat, a pig or a sheep.

The following examples are illustrative, and are not intended to limit the scope of the claims. The description of a composition or a method in an example does not imply that a described composition has, or has not, been produced, or that the described method has been performed, regardless of verb tense used.

EXAMPLES

Example 1

This example illustrates treatment of a knee injury.

In this example, an athletic patient presents with a traumatic knee injury to an orthopedic surgeon. A diagnosis is made of damaged articular cartilage of the femoral condyle. The surgeon performs a microfracture procedure on the patient's femoral condyle, creating channels through the bone underlying the hyaline cartilage. The surgeon selects a membrane comprising polyester entangled with hyaluronic acid, and shaped to follow the contours of the condyle. The polyester is a copolymer of lactic acid and polyglycolic acid in a weight ratio of 3:1 and has a weight average molecular weight of 100,000. The hyaluronic acid has an average molecular weight of 1,700,000. The weight ratio of polyester to hyaluronic acid is 9:1, and the membrane and has a thickness of 3 mm. The surgeon coats one side of the membrane with TISSEEL® VH fibrin sealant. She then applies the membrane to the damaged femoral condyle using gentle pressure. The patient is instructed to keep pressure off the knee for a period of weeks. The condyle is repaired with new hyaline cartilage by six months after the surgical intervention.

Example 2

This example illustrates treatment of osteoarthritis.

In this example, a patient with osteoarthritis presents with a full-thickness chondral defect in an elbow joint. The patient is operated upon by a surgeon, who performs a microfracture procedure on the humerus underlying the joint. A membrane comprising a polyester entangled with hyaluronic acid, and shaped to follow the contours of the condyle of the humerus, is then positioned by the surgeon upon the condyle. The polyester is a copolymer of lactic acid and polyglycolic acid in a weight ratio of 4:1 and has a weight average molecular weight of 100,000. The hyaluronic acid has a weight average molecular weight of 1,700,000. The weight ratio of polyester to hyaluronic acid is 8:1. The membrane has a thickness of 1 mm. The surgeon secures the membrane in place with a series of screws made of a resorbable PLA/PLG polymer. Following surgery, new hyaline cartilage deposits along the condyle over a six month period. The new cartilage is anatomically indistinguishable from normal hyaline cartilage.

Example 3

In this example, a middle age male presents with a traumatic dislocation of the shoulder. A diagnosis is made of disruption of the articular cartilage covering the head of the humerus at its articulation with the glenoid socket of the scapula. The patient is operated upon by a surgeon, who performs a microfracture procedure on the head of the humerus. A membrane comprising a polyester entangled with hyaluronic acid, and shaped to approximate the contours of the humeral head, is then positioned by the surgeon upon the humeral head. The polyester is a copolymer of lactic acid and polyglycolic acid in a weight ratio of 3:1 and has a weight average molecular weight of 200,000. The hyaluronic acid has a weight average molecular weight of 1,700,000. The weight ratio of polyester to hyaluronic acid is 9:1. The membrane has a thickness of 1 mm. The surgeon secures the membrane in place with a series of resorbable pins. Following surgery, new hyaline cartilage deposits along the condyle over a period of six months. The new cartilage is anatomically indistinguishable from normal hyaline cartilage.

Example 4

This example illustrates a method of constructing an entangled matrix comprising a polyester and a polysaccharide.

In this example, poly(lactide-co-glycolide) having molecular weight of $1.5 \times 10^6$ is dissolved in dichloromethane (125 mg/ml) and with Hyaluronate (HA) of molecular weight of about $1.3 \times 10^6$ Dalton is dissolved in water (15 mg/ml). The two polymer solutions, 2 parts PLGA, and 1 part HA, are mixed with 1 part Milli Q water by vortexing at high speed for about 5 minutes. The emulsified mixture is immediately poured into a mold pre-cooled at −70° C. in a bath containing dry ice in isopropyl alcohol. After freezing, the mold and its contents are transferred into a second container that is loaded with dry ice and connected to vacuum line. Organic solvent is removed by this process at the temperature between −70° C. to −40° C., leaving HA in wet-ice phase. Water is then removed by raising the temperature to −10° C. under vacuum.

All references cited in this specification are hereby incorporated by reference in their entireties. Any discussion of references cited herein is intended merely to summarize the assertions made by their authors and no admission is made that any reference or portion thereof constitutes relevant prior art. Applicants reserve the right to challenge the accuracy and pertinency of the cited references.

What is claimed is:

1. A method for repairing a full-thickness chondral defect of a joint of a patient in need of treatment, the method comprising:
    a) microfracturing bone underlying the joint;
    b) applying to the joint a membrane, wherein the membrane comprises a polyester polymer entangled with a hyaluronate polymer, at a weight ratio of polyester polymer to hyaluronate polymer of between 9:1 and 1:9, wherein the entanglement of the polymers is produced by forming an emulsified mixture of the polyester polymer in a first solvent and the hyaluronate polymer in a second solvent, adding the emulsified mixture to a mold, freezing the emulsified mixture in the mold, removing solvent from the resultant frozen mixture by vacuum, wherein the membrane has a thickness of at least 0.5 mm up to 3 mm; and
    c) anchoring the membrane to the joint.

2. The method in accordance with claim 1, for repairing a full-thickness chondral defect in a knee joint, an elbow joint, or a shoulder joint, wherein said microfracturing, applying and anchoring steps are carried out on the defective joint.

3. The method in accordance with claim 1, wherein the polyester polymers comprise a co-polymer comprising polylactic acid and polyglycolic acid.

4. The method in accordance with claim 2, wherein the polylactic acid and the polyglycolic acid are in a weight ratio of about 5:1 to about 2:1.

5. The method in accordance with claim 1, wherein the anchoring the membrane to the joint comprises applying at least one fastener which secures the membrane to the joint, wherein the at least one fastener is selected from the group consisting of a biocompatible glue, a suture, a tissue weld, a dart, a staple, a screw, and a tack.

6. A method for repairing a full-thickness chondral defect of a joint of a patient in need of treatment, the method comprising:
    a) introducing at least one aperture through bone underlying the joint, wherein the at least one aperture makes possible migration to the joint of mesenchymal stem cells comprised by a marrow cavity of the bone;
    b) applying to the joint a membrane, wherein the membrane comprises a polyester polymer entangled with a hyaluronate polymer, at a weight ratio of polyester polymer to hyaluronate polymer of between 9:1 and 1:9, wherein the entanglement of the polymers is produced by forming an emulsified mixture of the polyester polymer in a first solvent and the hyaluronate polymer in a second solvent, adding the emulsified mixture to a mold, freezing the emulsified mixture in the mold, removing solvent from the resultant frozen mixture by vacuum, wherein the membrane has a thickness of at least 0.5 mm up to 3 mm; and c) securing the membrane to the joint.

7. The method in accordance with claim 6, wherein the polyester polymers comprise a co-polymer comprising polylactic acid and polyglycolic acid.

8. The method in accordance with claim 7, wherein the polylactic acid and the polyglycolic acid are in a weight ratio of about 5:1 to about 2:1.

9. The method for repairing a hyaline cartilage defect in accordance with claim 6, wherein the securing the membrane to the joint comprises applying at least one fastener to the membrane and the joint, wherein the at least one fastener is selected from the group consisting of a biocompatible glue, a suture, a tissue weld, a dart, a staple, a screw, and a tack.

* * * * *